United States Patent [19]

Asakura et al.

[11] Patent Number: 5,725,797
[45] Date of Patent: Mar. 10, 1998

[54] SILACYCLOHEXANE COMPOUND, A PROCESS FOR PRODUCING THE SAME, AND A LIQUID CRYSTAL COMPOSITION COMPRISING THE SAME

[75] Inventors: Kazuyuki Asakura; Takanobu Takeda; Takaaki Shimizu; Tsutomu Ogihara; Tatsushi Kaneko, all of Kubiki-mura, Japan

[73] Assignee: Shin-Etsu Chemical Co., Ltd., Tokyo, Japan

[21] Appl. No.: 742,626

[22] Filed: Oct. 31, 1996

[30] Foreign Application Priority Data

Oct. 31, 1995 [JP] Japan ................................. 7-283011

[51] Int. Cl.$^6$ .......................... C09K 19/34; C09K 19/30; G02F 1/13
[52] U.S. Cl. .................... 252/299.61; 252/299.63; 349/182
[58] Field of Search ................ 252/299.01, 299.63, 252/299.61; 349/182

[56] References Cited

U.S. PATENT DOCUMENTS 5,370,819  12/1994  Fujita et al. ................. 252/299.01

FOREIGN PATENT DOCUMENTS

| 0597701 | 5/1994 | European Pat. Off. |
| 0665232 | 2/1995 | European Pat. Off. |
| 0668285 | 8/1995 | European Pat. Off. |
| 0668286 | 8/1995 | European Pat. Off. |
| 6-312946 | 11/1994 | Japan |

*Primary Examiner*—Shean C. Wu
*Attorney, Agent, or Firm*—McAulay Fisher Nissen Goldberg & Kiel, LLP

[57] ABSTRACT

For the purpose of improving the characteristics of a liquid crystal substance, there is provided a silacyclohexane compound represented by the general formula (I):

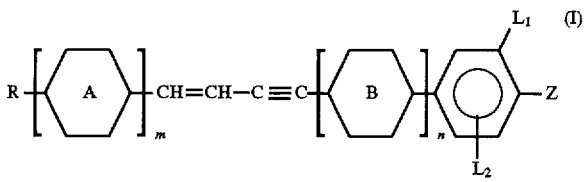

wherein R represents a specific straight-chain alkyl group, mono or difluoro alkyl group, branched-chain alkyl group, alkoxyalkyl group, and alkenyl group; at least one of rings A and B represent a trans-1-sila-1,4-cyclohexylene group or a trans-4-sila-1,4-cyclohexylene group both having a substituent group H, F, Cl, CH$_3$ or Ar (Ar stands for a phenyl or tolyl group) on silicon at the 1 or 4 position, and the other group, if any, represents a trans-1,4-cyclohexylene group or

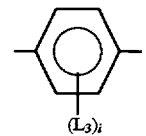

Z represents CN, F, Cl, CF$_3$, CClF$_2$, CHClF, OCF$_3$, OCClF$_2$, OCHF$_2$, OCHClF, R, or OR; L$_1$ represents H, F or Cl; L$_2$ and L$_3$ stand independently for H or F; i represents an integer of 0 to 2; m is 1 or 2; n is 0 or 1; and if m is 2, the two rings may be the same or different.

5 Claims, No Drawings

SILACYCLOHEXANE COMPOUND, A PROCESS FOR PRODUCING THE SAME, AND A LIQUID CRYSTAL COMPOSITION COMPRISING THE SAME

BACKGROUND OF THE INVENTION

1. Field of the Invention

The present invention relates to a novel silacyclohexane compound, a process for producing the same, a liquid crystal composition comprising the same, and a liquid crystal display element comprising said liquid crystal composition.

2. Description of the Related Art

The liquid crystal display element makes use of the optical anisotropy and dielectric anisotropy possessed by a liquid-crystal substance and is classified based on its display system into various types, such as a TN type (twisted nematic type), STN type (supertwisted nematic type), SBE type (superbirefringence type), DS type (dynamic scattering type), guest-host type, DAP type (deformed alignment phase), PD type (polymer dispersion type), and OMI type (optical mode interference type). The most common display device possesses a twisted nematic structure, which relies on the Shutt-Hellfritt effect.

The required properties of the liquid crystal composition used in such a liquid crystal display element vary depending on its display system, but common desirable properties for any display system include a broad temperature range of liquid crystal and stability in the presence of moisture, air, light, heat, electric fields, etc. Furthermore, the liquid crystal composition is required to possess low viscosity and provides a short address time, low threshold voltage and high contrast in a cell.

At present, there is no substance which as a single compound satisfies these requirements, therefore, a liquid mixture obtained by mixing several to more than ten liquid crystal compounds and potential liquid crystal compounds is used in practice. Therefore, easy miscibility among the constituents of a liquid crystal composition is one of the essential characteristics of such a substance.

Among the liquid crystal compounds which can serve as such a constituent, the following compound having an eneyne chain in its skeleton is known as a compound having low viscosity and a broad liquid crystal range (Japanese Patent Provisional Publication No. 312946/1994).

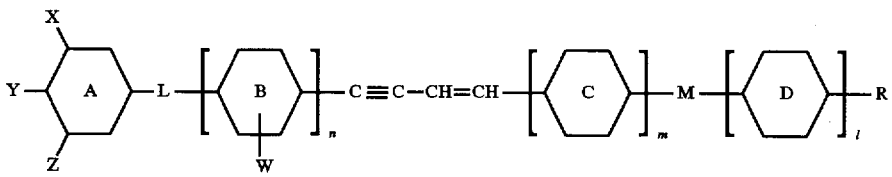

SUMMARY OF THE INVENTION

Recently, highly stringent characteristics are required for liquid crystal materials with their increasing application to liquid crystal displays. In particular, there is increasing demand for liquid crystal materials that are superior to conventional ones with respect to low driving voltage, a broad temperature range for use in automobiles, and improved low-temperature properties.

From this viewpoint, the present inventors have developed, for the first time, a liquid crystal substance having improved characteristics, and the object of such invention is to provide a liquid crystal compound having a Silacyclohexane ring completely different from the prior art liquid crystal compound having the eneyne chain in its skeleton as described above.

Accordingly, the present invention relates to a silacyclohexane compound represented by the general formula (I):

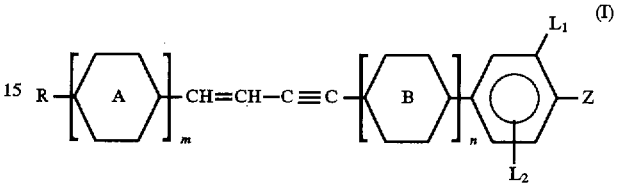

wherein R represents a straight-chain alkyl group having 1 to 10 carbon atoms, a mono or difluoro alkyl group having 1 to 10 carbon atoms, a branched-chain alkyl group having 3 to 8 carbon atoms, an alkoxyalkyl group having 2 to 7 carbon atoms, and an alkenyl group having 2 to 8 carbon atoms;

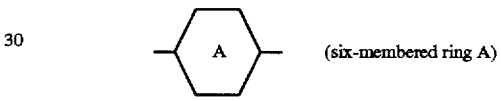

and

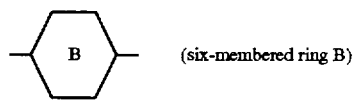

are groups selected from the group consisting of a trans-1-sila-1,4-cyclohexylene group and a trans-4-sila-1,4-cyclohexylene group both having a substituent group H, F, Cl, CH$_3$ or Ar (Ar stands for a phenyl or tolyl group) on silicon at the 1 or 4 position, a trans-1,4-cyclohexylene group, and

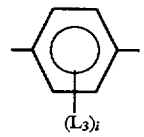

provided that at least one of the groups of the above six-membered ring expressed as A and the above six-membered ring expressed as B is a trans-1-sila-1,4- cyclohexylene or trans-4-sila-1,4-cyclohexylene group having a substituent group H, F, Cl, CH$_3$ or Ar (Ar stands for a phenyl or tolyl group) on silicon at the 1 or 4 position; Z represents CN, F, Cl, CF$_3$, CClF$_2$, CHClF, OCF$_3$, OCClF$_2$, OCHF$_2$, OCHClF, R, or OR; L$_1$ represents H, F or Cl; L$_2$ and L$_3$ stand independently for H or F; i represents an integer of 0 to 2; m is 1 or 2; n is 0 or 1; and if m is 2, the two rings are independent and may be either the same or different.

In addition, the present invention is directed towards a process for producing the silacyclohexane compound, which comprises a carbon-carbon bond forming reaction between an organometallic reagent represented by the following formula:

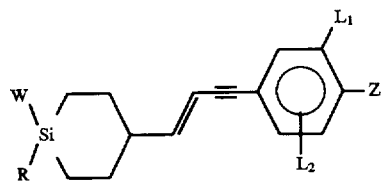

wherein M represents MgP or Li where P represents a halogen atom, and a compound represented by the following formula:

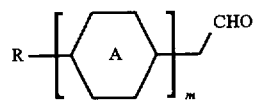

the product of which undergoes a hydrolysis reaction to form an alcohol compound, represented by the following formula:

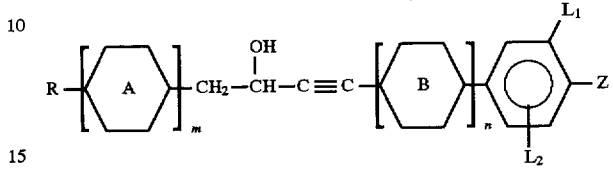

followed by a dehydration reaction of the alcohol compound to form the silacyclohexane compound.

Further, the present invention relates to a liquid crystal composition comprising a silacyclohexane compound represented by the general formula (I), as well as a liquid crystal element comprising said liquid crystal composition.

Hereinafter, the present invention is described in more detail.

The novel compound represented by the general formula (I) is specifically represented by any one of the ring structures shown in (A1) to (A82) and includes a silacyclohexane compound having at least one trans-1- or trans-4-silacyclohexane ring.

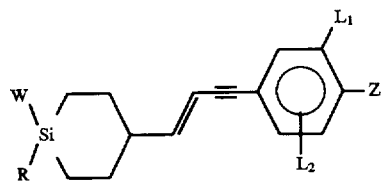
(A1)

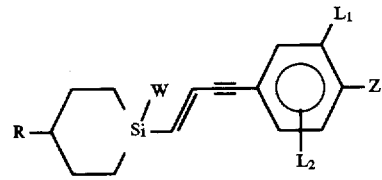
(A2)

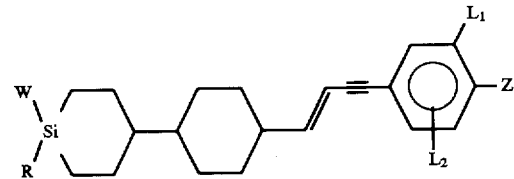
(A3)

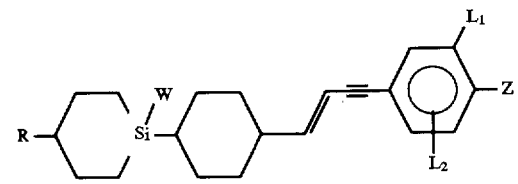
(A4)

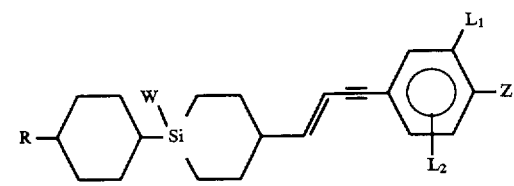
(A5)

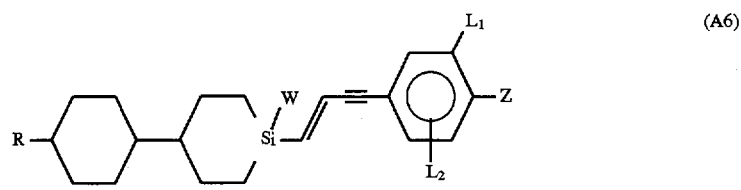 (A6)
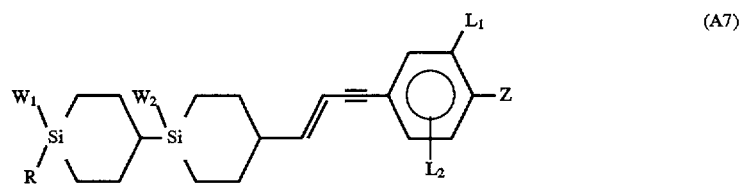 (A7)
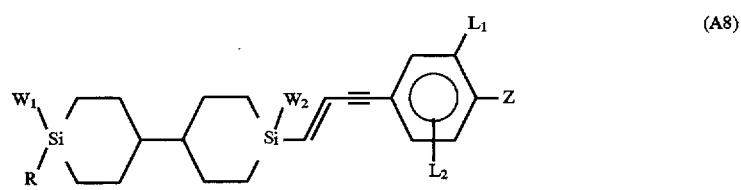 (A8)
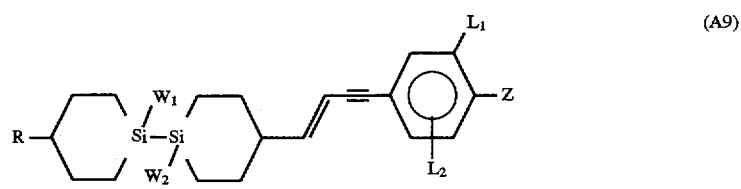 (A9)
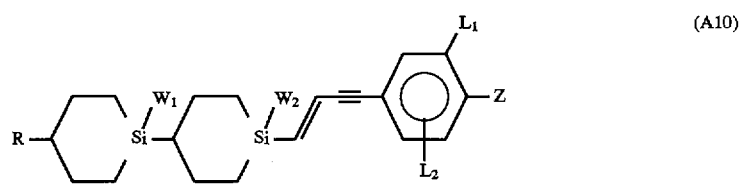 (A10)
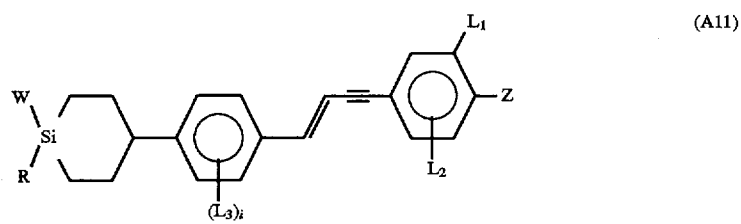 (A11)
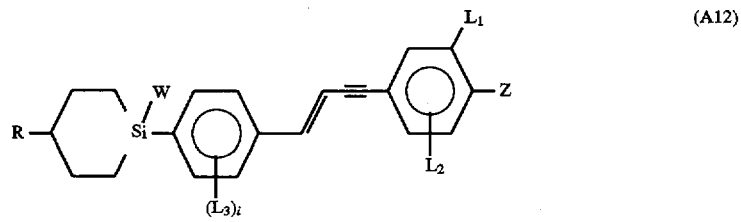 (A12)
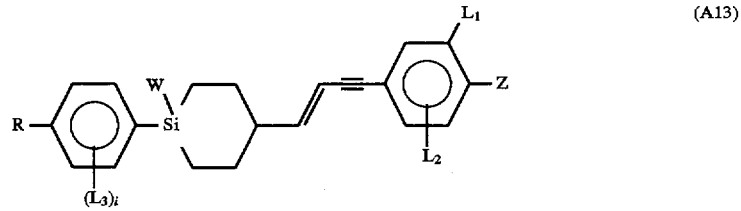 (A13)

-continued
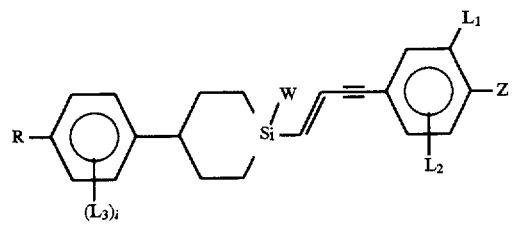 (A14)
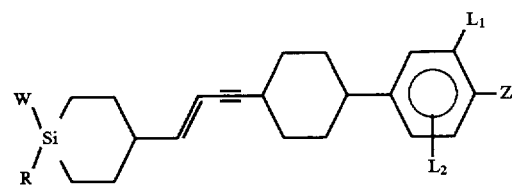 (A15)
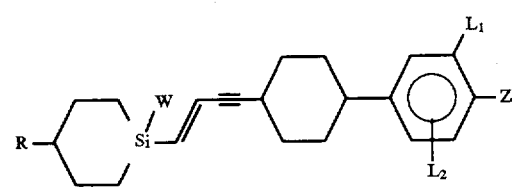 (A16)
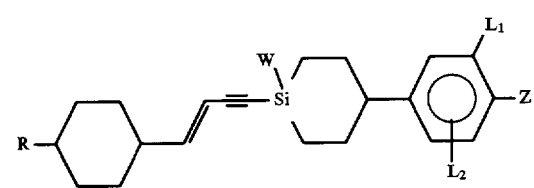 (A17)
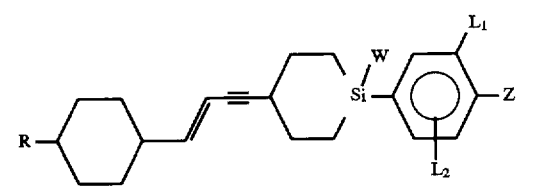 (A18)
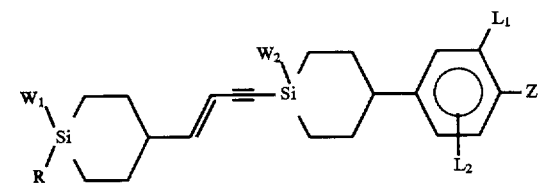 (A19)
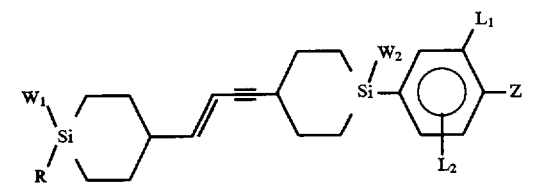 (A20)
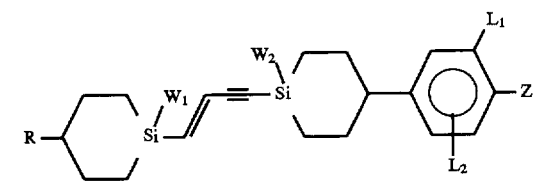 (A21)

-continued
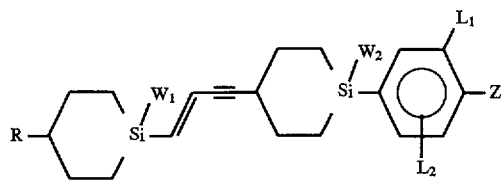 (A22)
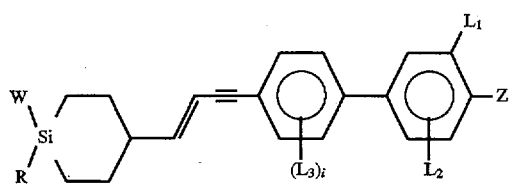 (A23)
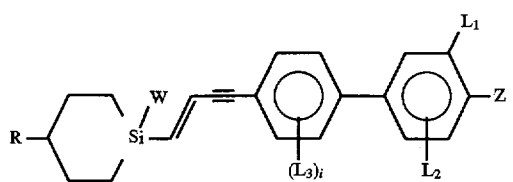 (A24)
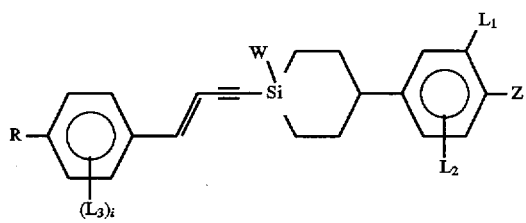 (A25)
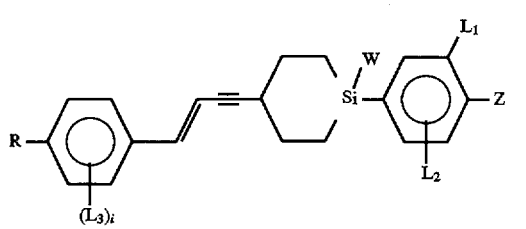 (A26)
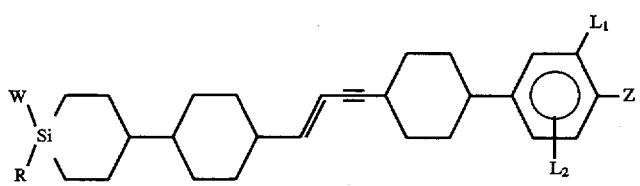 (A27)
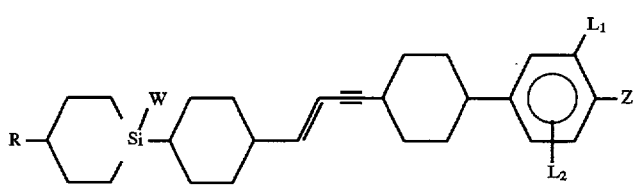 (A28)
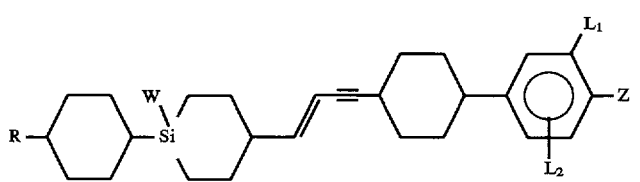 (A29)

-continued
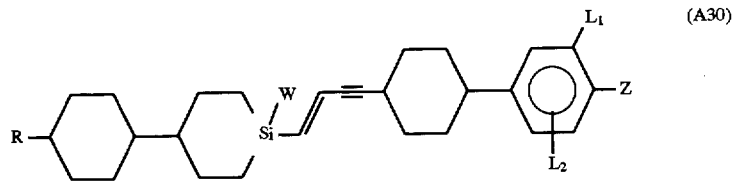 (A30)
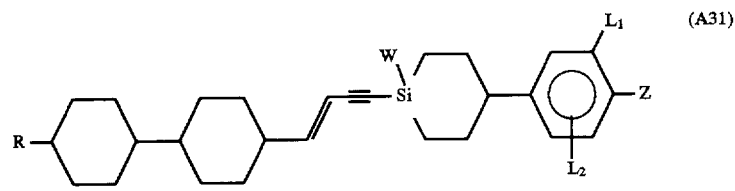 (A31)
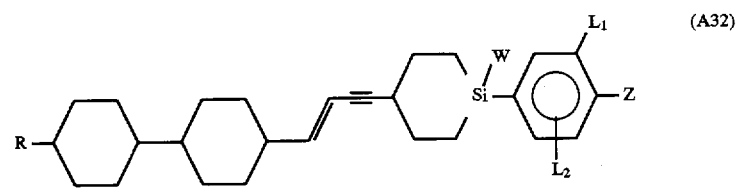 (A32)
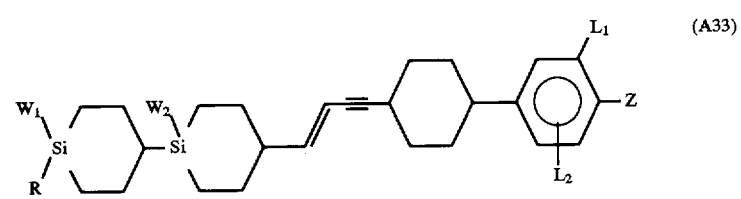 (A33)
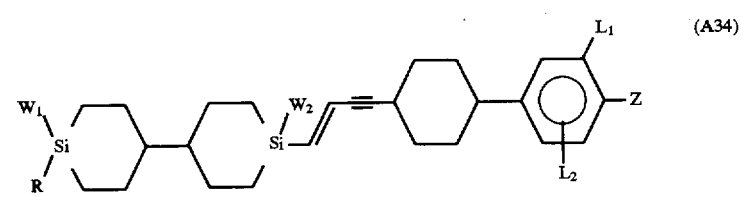 (A34)
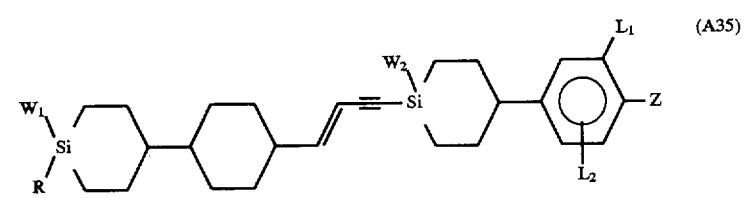 (A35)
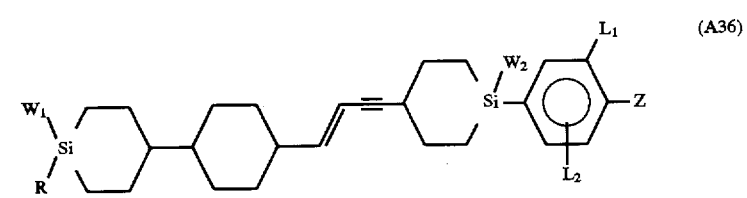 (A36)
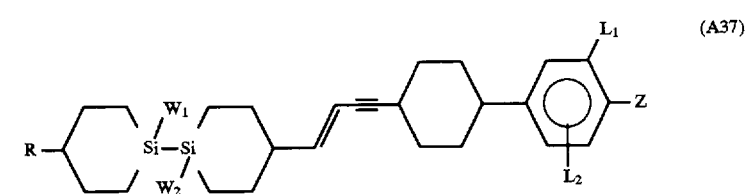 (A37)

-continued
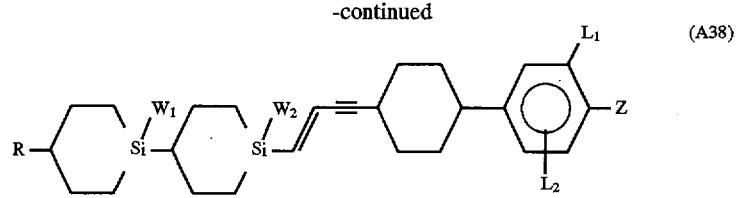 (A38)
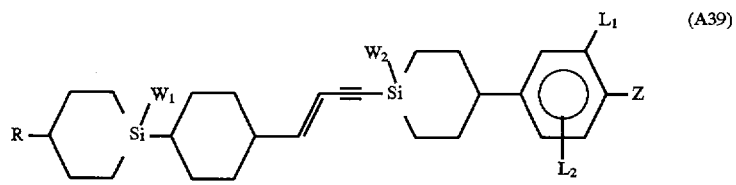 (A39)
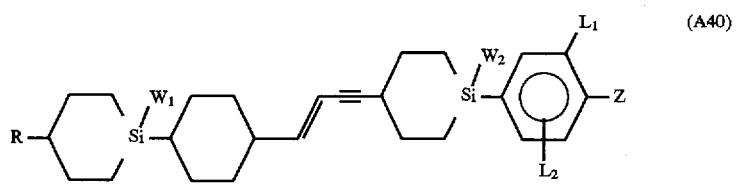 (A40)
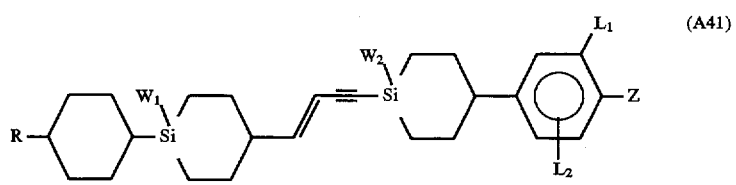 (A41)
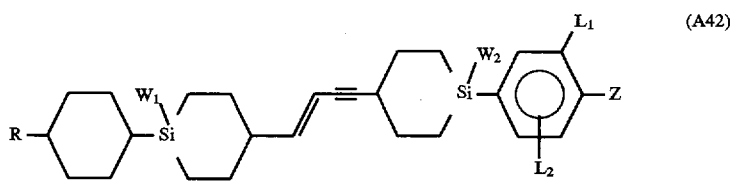 (A42)
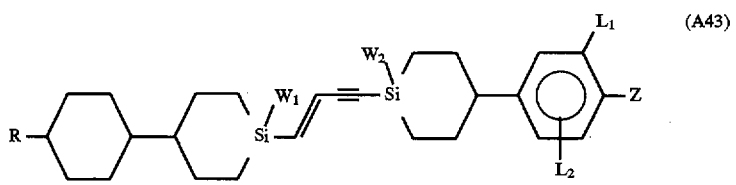 (A43)
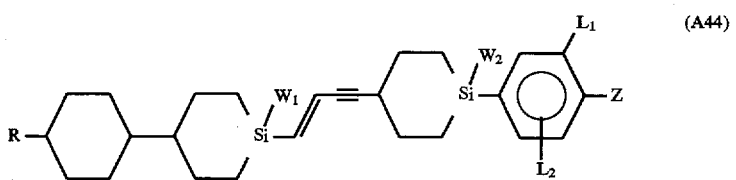 (A44)
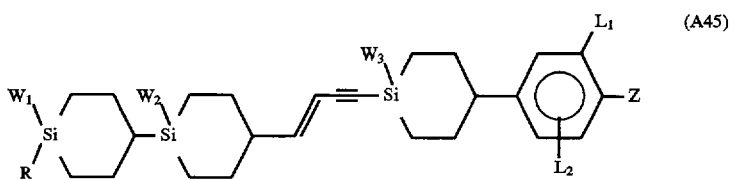 (A45)
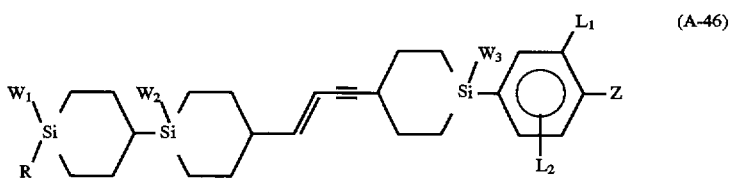 (A-46)

-continued
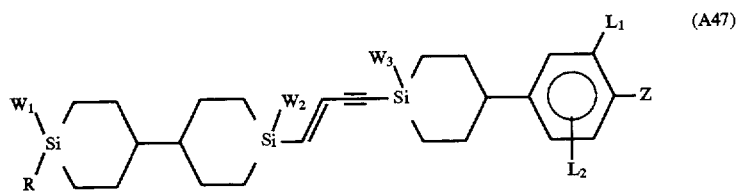 (A47)
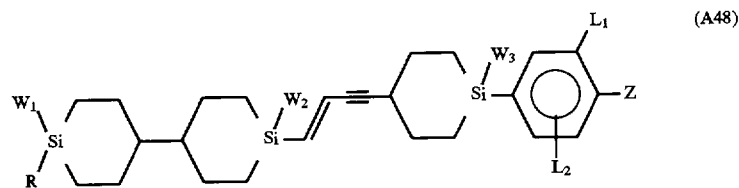 (A48)
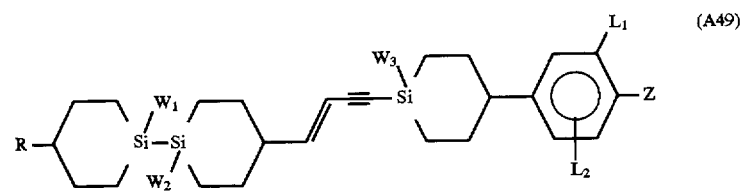 (A49)
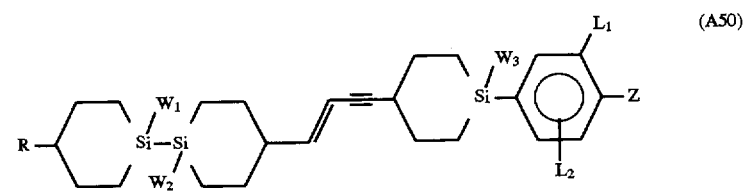 (A50)
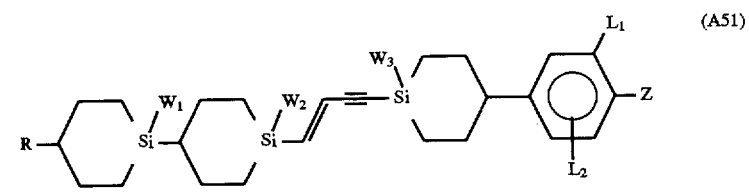 (A51)
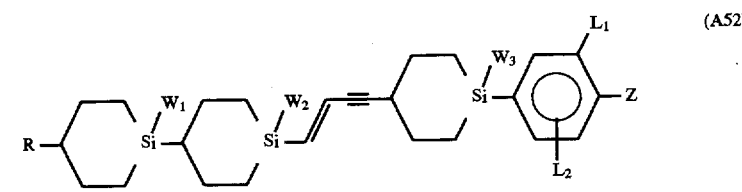 (A52)
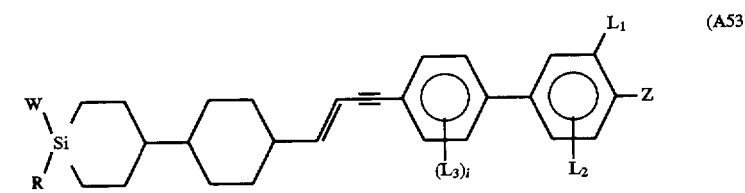 (A53)
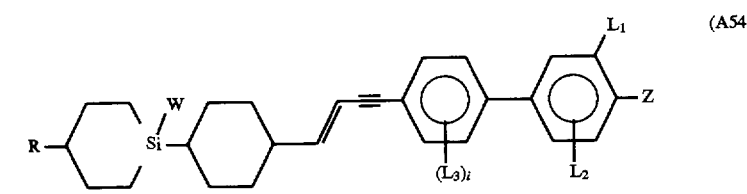 (A54)

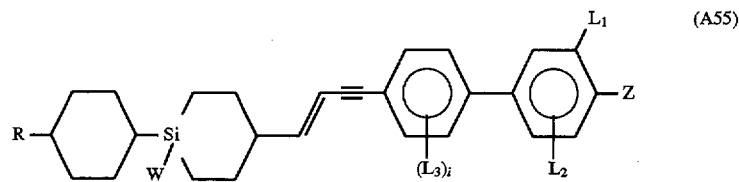 (A55)
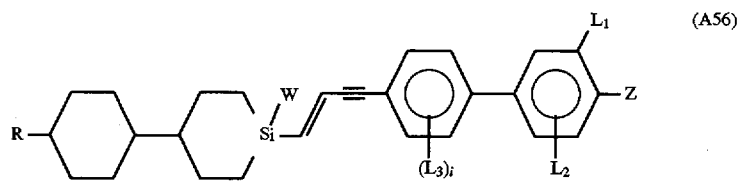 (A56)
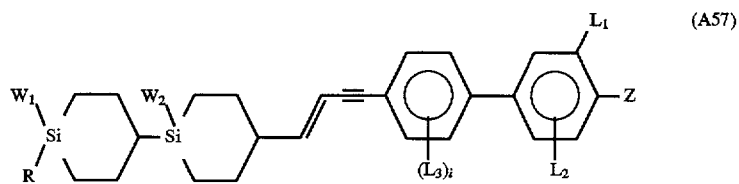 (A57)
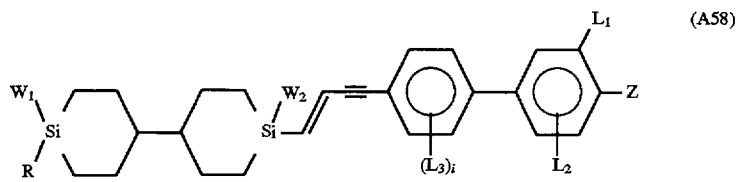 (A58)
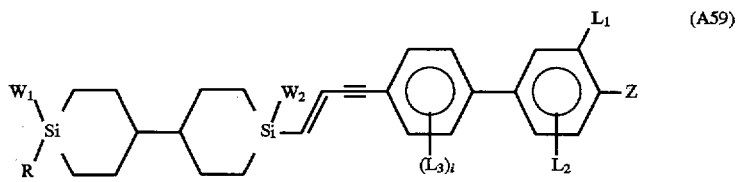 (A59)
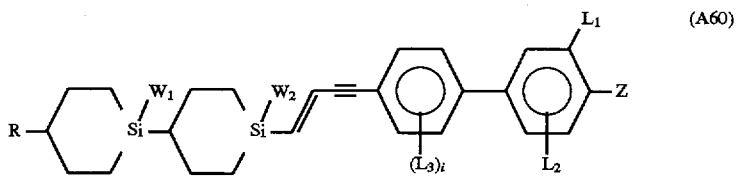 (A60)
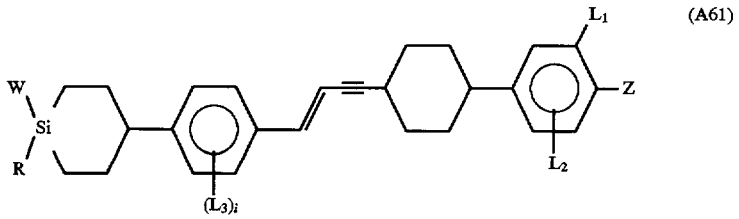 (A61)
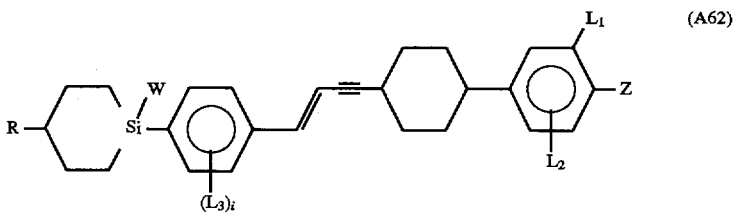 (A62)

-continued
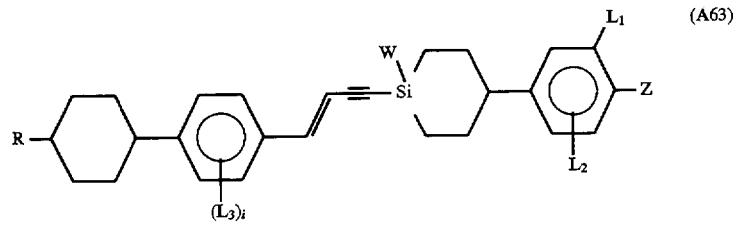 (A63)
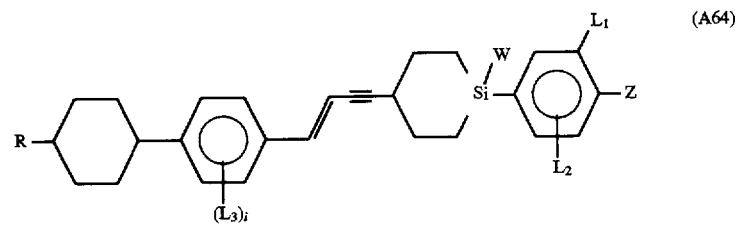 (A64)
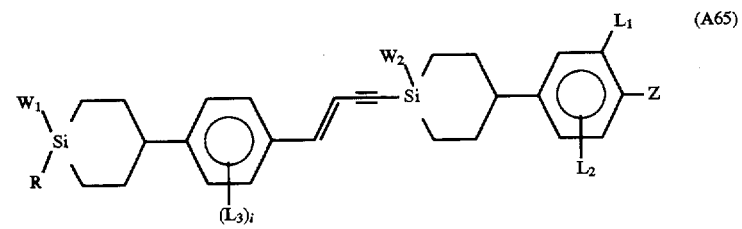 (A65)
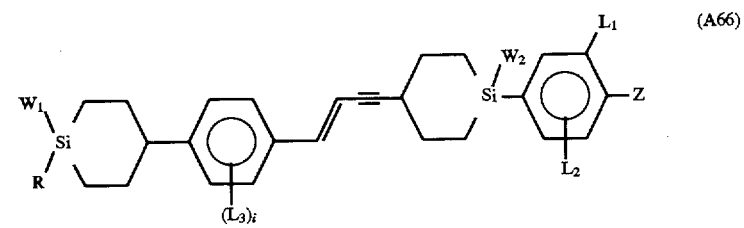 (A66)
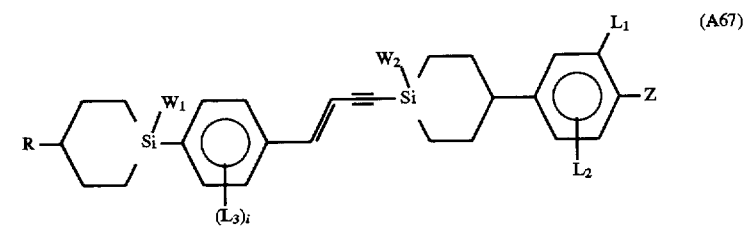 (A67)
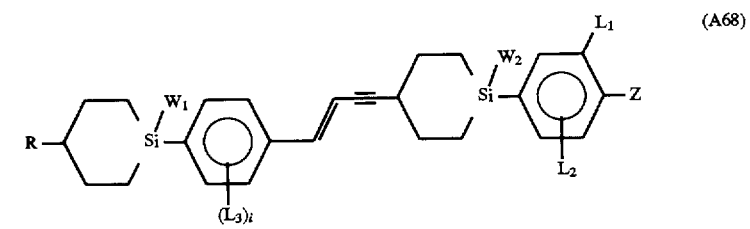 (A68)
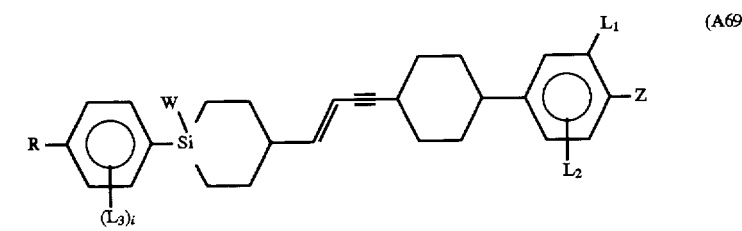 (A69)

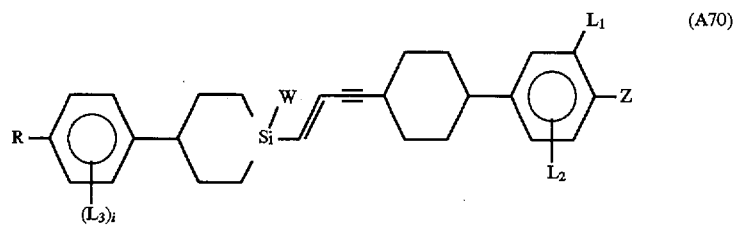
(A70)
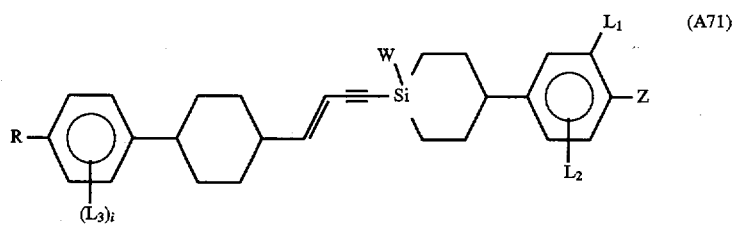
(A71)
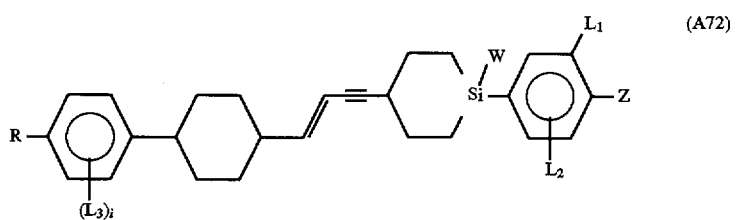
(A72)
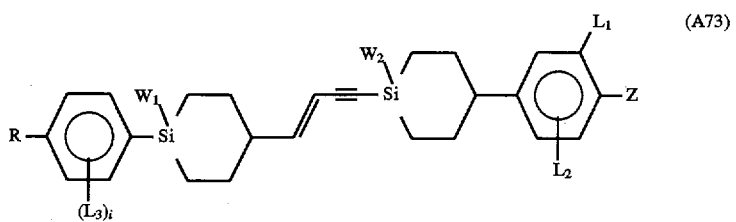
(A73)
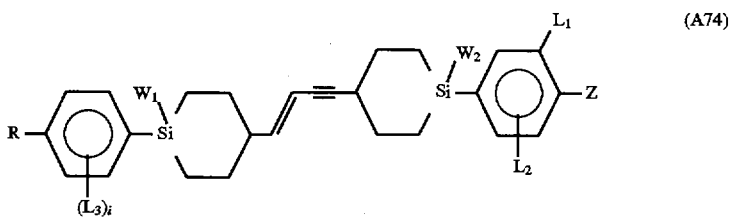
(A74)
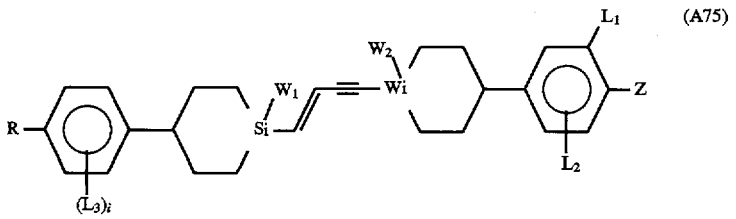
(A75)
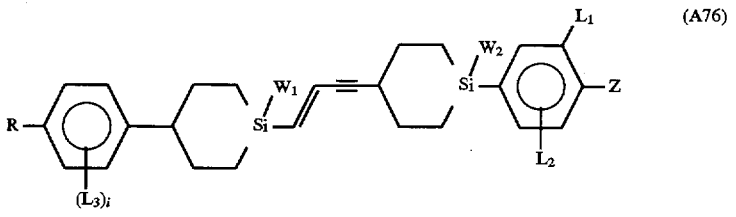
(A76)

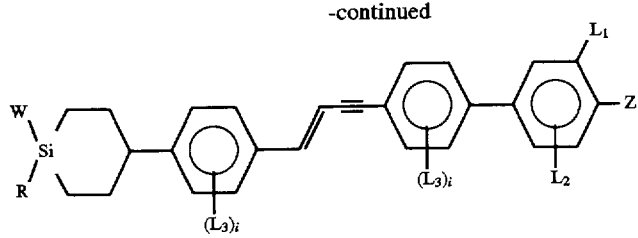
(A77)

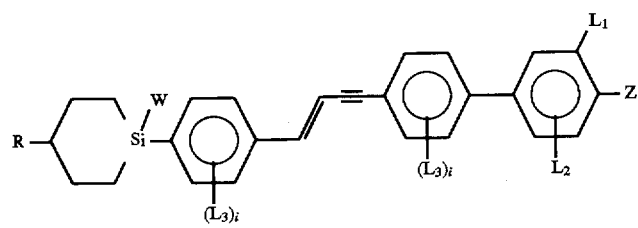
(A78)

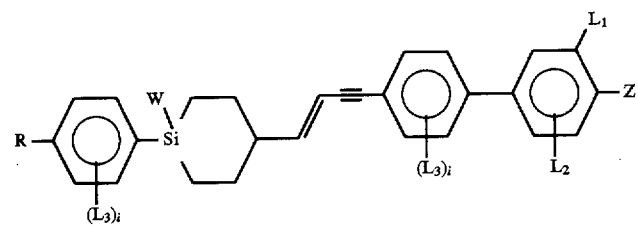
(A79)

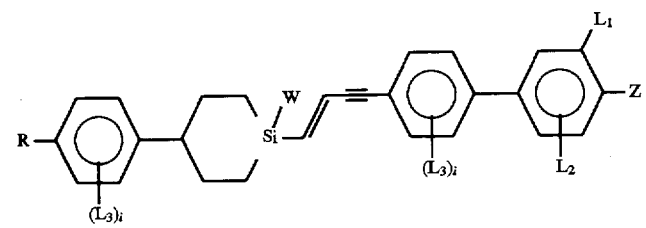
(A80)

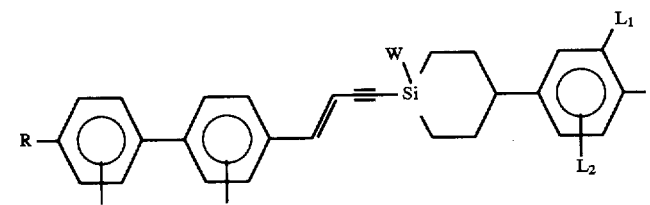
(A81)

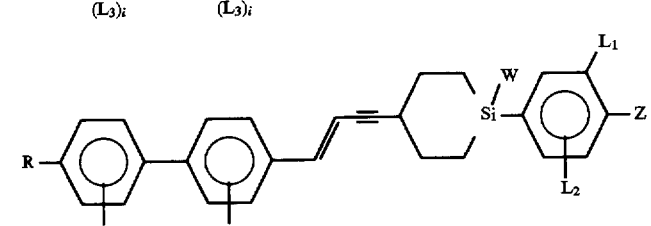
(A82)

In these chemical formulae, R stands for any one of the following groups (a) to (e):

(a) straight-chain alkyl groups having 1 to 10 carbon atoms, such as methyl group, ethyl group, n-propyl group, n-butyl group, n-pentyl group, n-hexyl group, n-heptyl group, n-octyl group, n-nonyl group, and n-decyl group;

(b) mono or difluoro alkyl groups having 1 to 10 carbon atoms, such as fluoromethyl group, 1-fluoroetyl group, 1-fluoropropyl group, 1-fluorobutyl group, 1-fluoropentyl group, 1-fluorohexyl group, 1-fluoroheptyl group, 1-fluorooctyl group, 1-fluorononyl group, 1-fluorodecyl group, 2-fluoroethyl group, 2-fluoropropyl group, 2-fluorobutyl group, 2-fluoropentyl group, 2-fluorohexyl group, 2-fluoroheptyl group, 2-fluorooctyl group, 2-fluorononyl group, 2-fluorodecyl group, 3-fluoropropyl group, 3-fluorobutyl group, 3-fluoropentyl group, 3-fluorohexyl group, 3-fluoroheptyl group, 3-fluorooctyl group, 3-fluorononyl group, 3-fluorodecyl group, 4-fluorobutyl group, 4-fluoropentyl group, 4-fluorohexyl group, 4-fluoroheptyl group, 4-fluorooctyl group, 4-fluorononyl group, 4-fluorodecyl group, 5-fluoropentyl group, 5-fluorohexyl group, 5-fluoroheptyl group, 5-fluorooctyl group, 5-fluorononyl group, 5-fluorodecyl group, 6-fluorohexyl group, 6-fluoroheptyl group, 6-fluorooctyl group, 6-fluorononyl group, 6-fluorodecyl group, 7-fluoroheptyl group, 7-fluorooctyl group, 7-fluorononyl group, 7-fluorodecyl group, 8-fluorooctyl group, 8-fluorononyl group, 8-fluorodecyl group, 9-fluorononyl group, 9-fluorodecyl group, 10-fluorodecyl group, difluoromethyl group, 1,1-difluoroethyl group, 1,1-difluoropropyl group, 1,1-difluorobutyl group, 1,1-difluoropentyl group, 1,1-difluorohexyl group, 1,1-difluoroheptyl group, 1,1-difluorooctyl group, 1,1-difluorononyl group, 1,1-difluorodecyl group, 2,2-difluoroethyl group, 2,2-difluoropropyl group, 2,2-difluorobutyl group, 2,2-difluoropentyl group, 2,2-difluorohexyl group, 2,2-difluoroheptyl group, 2,2-difluorooctyl group, 2,2-difluorononyl group, 2,2-difluorodecyl group, 3,3-difluoropropyl group, 3,3-difluorobutyl group, 3,3-difluoropentyl group, 3,3-difluorohexyl group, 3,3-difluoroheptyl group, 3,3-difluorooctyl group, 3,3-difluorononyl group, 3,3-difluorodecyl group, 4,4-difluorobutyl group, 4,4-difluoropentyl group, 4,4-difluorohexyl group, 4,4-difluoroheptyl group, 4,4-difluorooctyl group, 4,4-difluorononyl group, 4,4-difluorodecyl group, 5,5-difluoropentyl group, 5,5-difluorohexyl group, 5,5-difluoroheptyl group, 5,5-difluorooctyl group, 5,5-difluorononyl group, 5,5-difluorodecyl group, 6,6-difluorohexyl group, 6,6-difluoroheptyl group, 6,6-difluorooctyl group, 6,6-difluorononyl group, 6,6-difluorodecyl group, 7,7-difluoroheptyl group, 7,7-difluorooctyl group, 7,7-difluorononyl group, 7,7-difluorodecyl group, 8,8-difluorooctyl group, 8,8-difluorononyl group, 8,8-difluorodecyl group, 9,9-difluorononyl group, 9,9-difluorodecyl group, and 10,10-difluorodecyl group;

(c) branched-chain alkyl groups having 3 to 8 carbon atoms, such as isopropyl group, sec-butyl group, isobutyl group, 1-methylbutyl group, 2-methylbutyl group, 3-methylbutyl group, 1-methylpentyl group, 2-methylpentyl group, 3-methylpentyl group, 1-ethylpentyl group, 1-methylhexyl group, 2-methylhexyl group, 3-methylhexyl group, 2-ethylhexyl group, 3-ethylhexyl group, 1-methylheptyl group, 2-ethylheptyl group, and 3-methylheptyl group;

(d) alkoxyalkyl groups having 2 to 7 carbon atoms, such as methoxymethyl group, ethoxymethyl group, propoxymethyl group, butoxymethyl group, pentoxymethyl group, hexyloxymethyl group, methoxyethyl group, ethoxyethyl group, propoxyethyl group, butoxyethyl group, pentoxyethyl group, methoxypropyl group, ethoxypropyl group, propoxypropyl group, butoxypropyl group, methoxybutyl group, ethoxybutyl group, propoxybutyl group, methoxypentyl group, and ethoxypentyl group;

(e) alkenyl groups having 2 to 8 carbon atoms, such as vinyl group, 1-propenyl group, allyl group, 1-butenyl group, 3-butenyl group, isoprenyl group, 1-pentenyl group, 3-pentenyl group, 4-pentenyl group, dimethylallyl group, 1-hexenyl group, 3-hexenyl group, 5-hexenyl group, 1-heptenyl group, 3-heptenyl group, 6-heptenyl group, and 7-octenyl group, W, $W_1$, $W_2$, and $W_3$ stand independently for H, F, Cl, CH$_3$ or Ar (Ar stands for a phenyl group or a tolyl group). It is preferable that W, $W_1$, $W_2$, and $W_3$ stand independently for H, F, Cl, or CH$_3$. It is further preferable that they stand independently for H, F, or CH$_3$.

The substituent group Z on the aromatic ring represents CN, F, Cl, CF$_3$, CClF$_2$, CHClF, OCF$_3$, OCClF$_2$, OCHF$_2$, OCHClF, R or OR. $L_1$ represents H, F or Cl. $L_2$ and $L_3$ stand independently for H or F. i represents an integer of 0 to 2.

The formula (B) group includes, but is not limited to, any group of the following formulae (B1) to (B39):

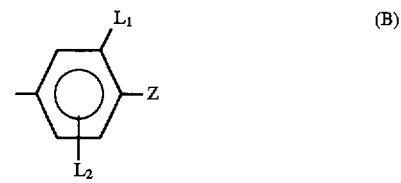

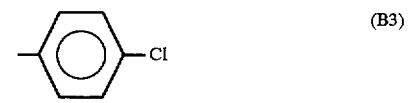

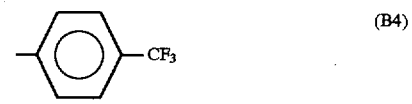

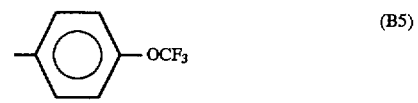

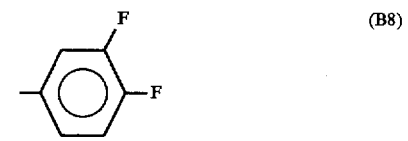

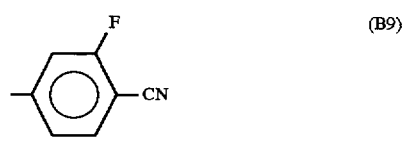

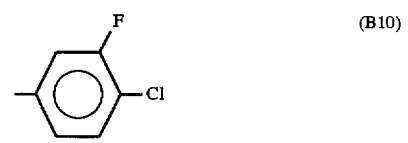

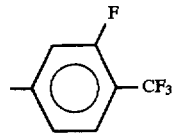 (B11)
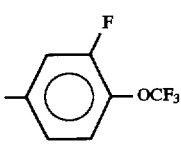 (B12)
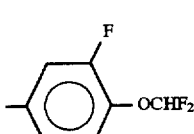 (B13)
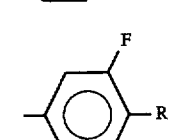 (B14)
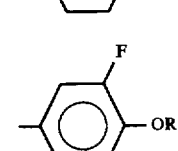 (B15)
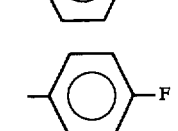 (B16)
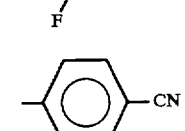 (B17)
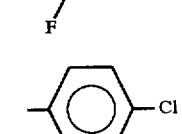 (B18)
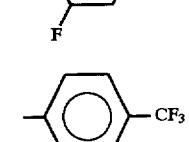 (B19)
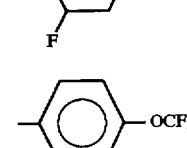 (B20)
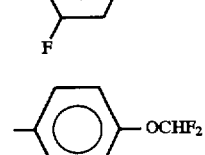 (B21)
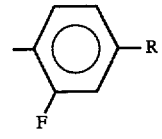 (B22)
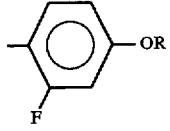 (B23)
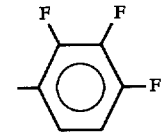 (B24)
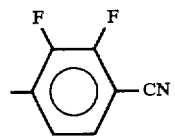 (B25)
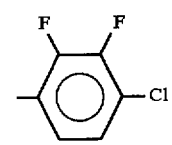 (B26)
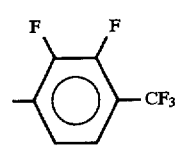 (B27)
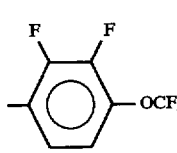 (B28)
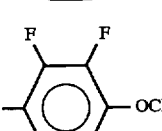 (B29)
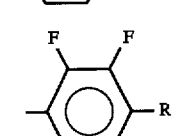 (B30)
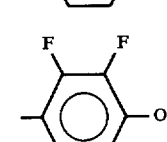 (B31)
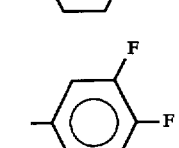 (B32)

-continued

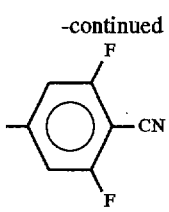 (B33)

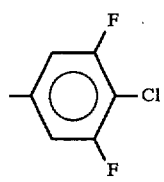 (B34)

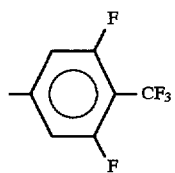 (B35)

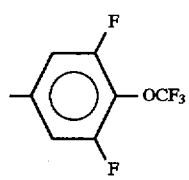 (B36)

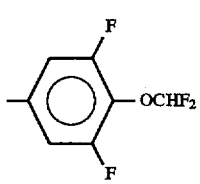 (B37)

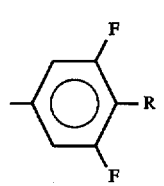 (B38)

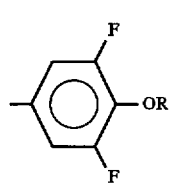 (B39)

The formula (C) group includes, but is not limited to, any group of the following formulae (C1) to (C7):

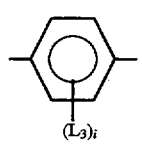 (C)

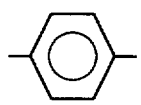 (C1)

-continued

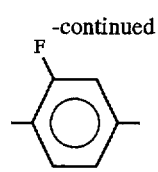 (C2)

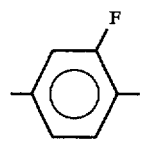 (C3)

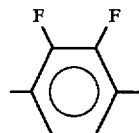 (C4)

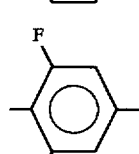 (C5)

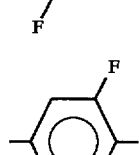 (C6)

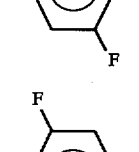 (C7)

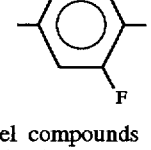

Out of the novel compounds of the formulae (A1) to (A82), represented by the general formula (I), the preferable compouds, with respect to the ring structure are: (A1), (A3), (A5), (A7), (A11), (A15), (A17), (A19), (A23), (A27), (A29), (A31), (A33), (A53), (A55), (A57), and (A77).

The R group is preferably any one of the following groups (a) to (e):

(a) straight-chain alkyl groups having 2 to 7 carbon atoms, among which, the preferable groups are the ethyl group, n-propyl group, n-butyl group, n-pentyl group, n-hexyl group, and n-heptyl group;

(b) mono or difluoro alkyl groups having 2 to 7 carbon atoms, among which, the preferable groups are the 2-fluoroethyl group, 2-fluoropropyl group, 2-fluorobutyl group, 2-fluoropentyl group, 2-fluorohexyl group, 2-fluoroheptyl group, 4-fluorobutyl group, 4-fluoropentyl group, 4-fluorohexyl group, 4-fluoroheptyl group, 5-fluoropentyl group, 5-fluorohexyl group, 5-fluoroheptyl group, 6-fluorohexyl group, 6-fluoroheptyl group, 7-fluoroheptyl group, 2,2-difluoroethyl group, 2,2-difluoropropyl group, 2,2-difluorobutyl group, 2,2-difluoropentyl group, 2,2-difluorohexyl group, 2,2-difluoroheptyl group, 4,4-difluorobutyl group, 4,4-difluoropentyl group, 4,4-difluorohexyl group, 4,4-difluoroheptyl group, 5,5-difluoropentyl group, 5,5-difluorohexyl group, 5,5-difluoroheptyl group, 6,6-difluorohexyl group, 6,6-difluoroheptyl group, and 7,7-difluoroheptyl group;

(c) branched-chain alkyl groups, among which, the preferable groups are the isopropyl group, 1-methylpropyl group, 2-methylpropyl group, 1-methylbutyl group, 2-methylbutyl group, 3-methylbutyl group, 1-methylpentyl group, 2-methylpentyl group, and 2-ethylhexyl group;

(d) alkoxyalkyl groups having 2 to 6 carbon atoms, among which, the preferable groups are the methoxymethyl group, methoxyethyl group, methoxypropyl group, methoxypentyl group, ethoxymethyl group, propoxymethyl group, and pentoxymethyl group; and (e) alkenyl groups having 2 to 8 carbon atoms, among which, the preferable groups are the vinyl group, 1-propenyl group, 3-butenyl group, 1-pentenyl group, 3-pentenyl group, 4-pentenyl group, 1-hexenyl group, 5-hexenyl group, 6-heptenyl group, and 7-octenyl group.

W, $W_1$, $W_2$, and $W_3$ are more preferably of the group H, F or $CH_3$.

Regarding the formula (B) group, (B1) to (B13), (22), (B23), (B30) to (B32), and (B34) to (B37) are preferable. Regarding the formula (C) group, (C1), (C3), (C4), and (C6) are preferable.

Further, the carbon chain containing the eneyne structure can be composed of isomers, with respect to the double bond. The E-stereoisomer, with respect to the double bond, can be useful as liquid crystal material.

The above compounds are produced by reacting an organometallic reagent with an aldehyde compound to form a carbon-carbon bond therebetween, then hydrolyzing the product into an alcohol compound and dehydrating the alcohol compound.

Hereinafter, this process is described in detail.

A carbon-carbon bond is formed by the reaction between the organometallic reagent (1) and the compound (2) and then the product is hydrolyzed to give the alcohol compound (3) which is then dehydrated. This dehydration can be effected using a catalyst such as mineral acid (sulfuric acid etc.), alkylsulfonic acid, arylsulfonic acid, thionyl chloride, etc. The solvent that can be used include hydrocarbons such as benzene, toluene, xylene, hexane, heptane, octane, etc., and oxygen-containing solvents such as diethyl ether, dibutyl ether, ethyl acetate, etc.

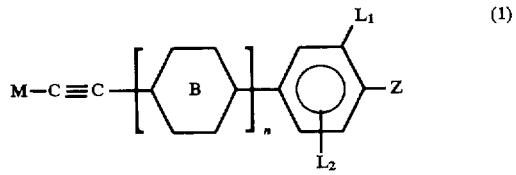
(1)

wherein M represents MgP or Li, and where P represents a hydrogen atom.

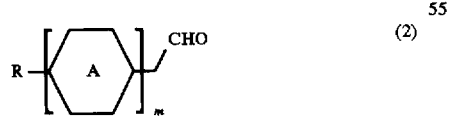
(2)

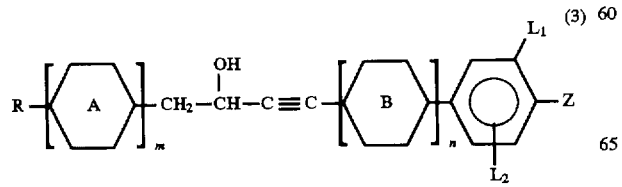
(3)

The organometallic reagent represented by formula (1) can be prepared by allowing an acetylene derivative represented by the following formula:

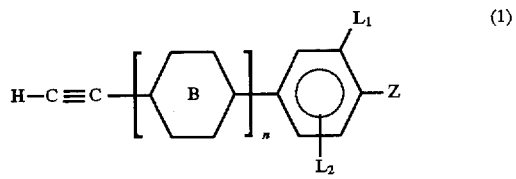
(1)

to react with alkyl metal compound such as n-butyllithium, s-butyllithium, t-butyllithium, methyllithium, methyl magnesium bromide, methyl magnesium chloride, ethyl magnesium bromide, n-butyl magnesium bromide, n-butyl magnesium chloride, etc., in a solvent such as tetrahydrofuran, diethyl ether, hexane, heptane etc., or with an alkali metal such as sodium, potassium, etc., in liquid ammonia, or with sodium hydride, potassium hydride, sodium amide, lithium amide, etc., in an inert solvent such as dimethylsulfoxide, dimethylformamide, tetrahydrofuran, etc.

The organometallic reagent thus obtained can be converted in-situ or in a suitable solvent into an aldehyde derivative represented by formula (2), followed by hydrolysis thereof into an alcohol compound represented by formula (3). Specifically, this reaction is carried out under cooling at a temperature of 30° C. or less, preferably in the range of −60° C. to 20° C. The reaction solvent includes tetrahydrofuran, dioxane, ether, benzene, toluene, xylene, hexane, heptane, octane, dimethylformamide, dimethylsulfoxide, etc.

If the compound thus formed is not only a mixture of trans- and cis-stereoisomers, with respect to the silacyclohexane and cyclohexane rings, but, also a mixture of E- and Z-isomers, with respect to the double bond, then the product which is both the trans-stereoisomer, with respect to the silacyclohexane and cyclohexane rings, and the E-isomer, with respect to the double bond, is separated and purified by conventional purification means such as chromatography, recrystallization etc., whereby the silacyclohexane compound of the present invention represented by the general formula (I) is obtained.

The silacyclohexane compound of the present invention can be mixed with a conventional compound to form a liquid crystal composition. The specific compound to be mixed for preparation of a liquid crystal composition can be selected from the following known compounds of formula (4) and (5):

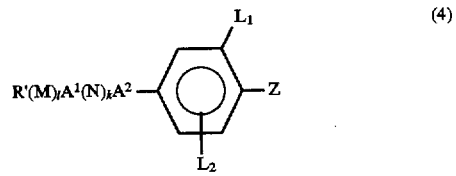
(4)

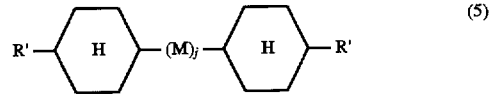
(5)

(M) and (N) in formulae (4) and (5) represent any one of the following groups (i) to (v):

(i) a trans-1,4-cyclohexylene group optionally substituted with one or more substituent groups selected from F, Cl, Br, CN, and an alkyl group;

(ii) a trans-1,4-cyclohexylene group where in the cyclohexane ring, one $CH_2$ group or two $CH_2$ groups not adjacent to each other, are replaced by O or S;

(iii) a 1,4-cyclohexylene group;

(iv) a 1,4-phenylene group optionally substituted with one or two substituent groups selected from F, Cl, $CH_3$ and CN; and (v) a 1,4-phenylene group where in the ring, one or two CH groups is replaced by N atoms.

$A^1$ and $A^2$ represent —$CH_2CH_2$—, —CH=CH—, —C≡C—, —$CO_2$—, —OCO—, —$CH_2O$—, —$OCH_2$— or a single bond.

l and k represents 0, 1, or 2 with proviso that l+k=1, 2, or 3; and j is 0, 1, or 2.

R' is hydrogen, a straight-chain alkyl group having 1 to 10 carbon atoms, a mono or difluoro alkyl group having 1 to 10 carbon atoms, a branched-chain alkyl group having 3 to 8 carbon atoms, an alkoxyalkyl group having 2 to 7 carbon atoms, or an alkenyl group having 2 to 8 carbon atoms.

$L_1$, $L_2$, and Z have the same meanings as defined above in the general formula (I).

In the foregoing, if both l and j are 2, a heterocyclic ring may be represented in (M). If k is 2, a heterocyclic ring may be represented in (N).

The proportion of one or more silacyclohexane compounds of the present invention in the liquid crystal phase is 1 to 50 mol %, preferably 5 to 30 mol %. The liquid crystal composition may further contain a multi-color dye for forming a colored guest-host system or additives for changing dielectric anisotropy, viscosity, or nematic phase orientation.

The liquid crystal composition thus formed can be used in a usual manner to produce a wide variety of liquid crystal display elements. Therefore, the liquid crystal composition containing one or more silacyclohexane compounds of the present invention is used as a liquid crystal display element by sealing it between transparent substrates provided with an electrode having a desired shape. This element may possess undercoats, overcoats for orientation regulation, in addition to polarization plates, filters, reflection layers etc. Moreover, the element may be used as a multilayer cell, or can be combined with a wide variety of other display elements or with a semiconductor substrate or a light source.

For driving the liquid crystal display element, it is possible to employ a dynamics scattering (DSM) system, twisted nematic (TN) system, supertwisted nematic (STN) system, polymer dispersion (PD) system, guest-host (GH) system, etc., known in the field of liquid crystal display elements.

The liquid crystal compound of the present invention in which Si is introduced as a ring-forming element possesses low viscosity, a wide liquid crystal range, and excellent compatibility. It can provide material which are widely applicable by replacing substituent groups on the skeleton containing the eneyne chain and on the terminal ring structure. Further, it can provide materials with a moderate to relatively high Δn value by selecting substituent groups on the skeleton structure and on the terminal ring. In addition, the liquid crystal compound of the present invention is stable in the environment where the liquid crystal element is used, and undergoes no deterioration even under such conditions as electromagnetic irradiation, the application of voltage, etc. When the liquid crystal compound of the present invention is used as a component in a liquid crystal composition, it has excellence in compatibility with other liquid crystal materials, thus making it possible to constitute a new liquid crystal display element having useful characteristics.

DETAILED DESCRIPTION OF PREFERRED EMBODIMENTS

The present invention is described in more detail with reference to the following examples.

EXAMPLE 1

Production of 1-(4-flurophenyl)-4-(trans-4-pentyl-4-silacyclohexyl)-1-butyne-3-ol Methyl magnesium chloride was prepared from magnesium 1.0 g (40 mmol) and methyl chloride 2.2 g (44 mmol) in 12 ml THF. This methyl magnesium chloride was added dropwise to a mixture of 4-ethynylfluorobenzene 5.76 g (48 mmol) and 100 ml THF at 20° to 30° C. for about 10 minutes.

The mixture was stirred for 30 minutes and then 4.3 g (20 mmol) 4-pentyl-4-silacyclohexyl acetaldehyde was added dropwise to it at 20° to 30° C. for about 10 minutes. After 1 hour aging at room temperature, it was cooled to 10° C. or less, followed by the addition of an aqueous solution of ammonium chloride. The sample was then subjected to a conventional post-treatment to give 7.7 g of 1-(4-fluorophenyl)-4-(trans-4-pentyl-4-silacyclohexyl)-1-butyne-3-ol.

The physical properties (IR and NMR) of the product were as follows:

IR $v_{max}$: 3342, 2958, 2921, 2854, 2103, 1602, 1508, 1457, 1409, 1234, 1189, 1155, 1091, 837, 786, 763 $cm^{-1}$.

1H-NMR (1000 MHz, $CDCl_3$) δ: 0.40–0.95 (11H, m), 1.15–1.50 (11H, m), 1.95 (1H, s), 3.75 (1H, s), 4.65 (1H, t), 7.00 (2H, m), 7.40 (2H, m).

EXAMPLE 2

Production of 1-(4-flurophenyl)-4-(trans-4-pentyl-4-silacyclohexyl)-3E-butene-1-yne A mixture of 1-(4-fluorophenyl)-4-(trans-4-pentyl-4-silacyclohexyl)-1-butyne-3-ol 8.0 g (24 mmol), p-toluenesulfonic acid monohydrate 1.6 g, and benzene 200 ml was heated under reflux to remove the water and then subjected to a conventional post-treatment. The reaction mixture thus obtained was not only a mixture of trans- and cis-isomers, with respect to the silacyclohexane ring, but also a mixture of E- and Z-isomers, with respect to the double bond. Hence, the product was separated by chromatography to give 1.2 g of the desired product of the trans-E isomer (yield 15.9%).

The physical properties (IR, NMR etc.) of the product were as follows:

IR $v_{max}$: 2956, 2919, 2853, 2102, 1601, 1506, 1457, 1407, 1230, 1155, 1092, 979, 950, 889, 835, 761, 709, 659 $cm^{-1}$.

1H-NMR (100 MHz, $CDCl_3$) δ: 0.40–0.95 (11H, m), 1.20–1.70 (8H, m), 1.80–2.15 (1H, m), 3.75 (1H, s), 5.65 (1H, d), 6.20 (1H, m), 6.85–7.10 (2H, m), 7.30–7.50 (2H, m). C-N transition temperature: 28.5° C. N-I transition temperature: 36.5° C.

The following compounds could be prepared in the same manner as in Example 1 by selecting suitable starting materials. Accordingly, the products are (P1) 1-(4-cyanophenyl)-4-(trans-4-proply-4-silacyclohexyl)-1-butyne-3-ol from 4-ethynylbenzonitrile and 4-propyl-4-silacyclohexylacetaldehyde, (P2) 1-(4-chlorophenyl)-4-(trans-4-propyl-4-silacyclohexyl)-1-butyne-3-ol from 4-ethynylchlorobenzene and 4-propyl-4-silacyclohexylacetaldehyde, (P3) 1-(4-trifluoromethylphenyl)-4-(trans-4-heptyl-4-silacyclohexyl)-1-butyne-3-ol from 4-ethynyltrifluoromethylbenzene and 4-heptyl-4-silacyclohexylacetaldehyde, (P4) 1-(4-trifluoromethoxyphenyl)-4-(trans-4-propyl-4-silacyclohexyl)-1-butyne-3-ol from 4-ethynyltrifluoromethoxybenzene and 4-propyl-4-silacyclohexylacetaldehyde, (P5) 1-(4-methoxyphenyl)-4-(trans-4-propyl-4-silacyclohexyl)-1-butyne-3-ol from 4-ethynylanisol and 4-propyl-4-silacyclohexylacetaldehyde, (P6) 1-(3,4-difluorophenyl)-4-(trans-4-propyl-4-fluoro-4-silacyclohexyl)-1-butyne-3-ol from 3,4-difluoroethynylbenzene and 4-propyl-4-fluoro-4-silacyclohexylacetaldehyde, (P7) 1-(3-fluoro-4-trifluoromethoxyphenyl)-4-(trans-4-propyl-4-methyl-4-silacyclohexyl)-1-butyne-3-ol from 3-fluoro-4-ethynyltrifluoromethoxybenzene and 4-methyl-4-propyl-4-silacyclohexylacetaldehyde, (P8) 1-(4-methylphenyl)-4-(trans-4-(5-methoxypentyl)-4-silacyclohexyl)-1-butyne-3-ol from 4-ethynyltoluene and 4-(5-methoxypentyl)-4-silacyclohexylacetaldehyde, (P9) 1-(3,4-difluorophenyl)-4-(trans-4-(4-pentenyl)-4-silacyclohexyl)-1-butyne-3-ol from 3,4-difluoroethynylbenzene and 4-(4-pentenyl)-4-silacyclohexylacetaldehyde, (P10) 1-(3-fluoro-4-cyanophenyl)-4-(trans-4-(3-methylbutyl)-4-silacylohexyl)-1-butyne-3-ol from 2-fluoro-4-ethynylbenzonitrile and 4-(3-methylbutyl)-4-silacyclohexylacetaldehyde, (P11) 1-(3-fluoro-4-trifluoromethylphenyl)-4-(trans-4-(4,4-difluorobutyl)-4-silacyclohexyl)-1-butyne-3-ol from 2-fluoro-4-ethynyltoluene and 4-(4,4-difluorobutyl)-4-silacyclohexylacetaldehyde, (P12) 1-(3-fluoro-4-trifluoromethoxyphenyl)-4-(trans-4-(4-fluoropentyl)-4-silacylohexyl)-1-butyne-3-ol from 2-fluoro-4-ethynyltrifluoromethoxybenzene and 4-(4-fluoropentyl)-4-silacyclohexylacetaldehyde, (P13) 1-(3-fluoro-4-difluoromethoxyphenyl)-4-(trans-4-(4,4-difluoropropyl)-4-silacyclohexyl)-1-butyne-3-ol from 2-fluoro-4-ethynyldifluoromethoxybenzene and 4-(4,4-difluoropropyl)-4-silacyclohexylacetaldehyde, (P14) 1-(4-fluorophenyl)-4-(trans-4-(trans-4-pentyl-4-silacyclohexyl)cyclohexyl)-1-butyne-3-ol from 4-ethynylfluorobenzene and 4-(4-pentyl-4-silacyclohexyl)cyclohexylacetaldehyde, (P15) 1-(2,3-difluoro- 4-trifluoromethylphenyl)-4-(trans-4-(trans-4-heptyl-4-silacyclohexyl)cyclohexyl)-1-butyne-3-ol from 2,3-difluoro-4-ethynyltrifluoromethylbenzene and 4-heptyl-4-silacyclohexylacetaldehyde, (P16) 1-(4-fluorophenyl)-4-(4-(trans-4-pentyl-4-silacyclohexyl)phenyl)-1-butyne-3-ol from 4-ethynylfluorobenzene and 4-(4-pentyl-4-silacyclohexyl)phenylacetaldehyde, (P17) 1-(3,4,5-trifluorophenyl)-4-(4-(trans-4-heptyl-4-silacyclohexyl)phenyl)-1-butyne-3-ol from 3,4,5-trifluoroethynylbenzene and 4-(4-heptyl-4-silacyclohexyl)phenylacetaldehyde, (P18) 1-(trans-4-(4-fluorophenyl)cyclohexyl)-4-(trans-4-pentyl-4-silacyclohexyl)-1-butyne-3-ol from 4-(4-ethynylcyclohexyl)fluorobenzene and 4-pentyl-4-silacyclohexylacetaldehyde, (P19) 1-(trans-4-(3,5-difluoro-4-trifluoromethylphenyl)cyclohexyl)-4-(trans-4-heptyl-4-silacyclohexyl)-1-butyne-3-ol from 4-(4-ethynylcyclohexyl)-2,6-difluorotrifluoromethylbenzene and 4-heptyl-4-silacyclohexylacetaldehyde, (P20) 1-(4'-fluoro-4-biphenyl)-4-(trans-4-pentyl-4-silacyclohexyl)-1-butyne-3-ol from 4-ethynyl-4'-fluorobiphenyl and 4-pentyl-4-silacyclohexylacetaldehyde, (P21) 1-(2,3',5'-trifluoro-4'-trifluoromethoxy-4-biphenyl)-4-(trans-4-pentyl-4-silacyclohexyl)-1-butyne-3-ol from 4-ethynyl-2,3'5'-trifluoro-4'-trifluoromethoxybiphenyl and 4-pentyl-4-silacyclohexylacetaldehyde, (P22) 1-(2,3,3',4',5'-pentafluoro- 4-biphenyl)-4-(trans-4-pentyl-4-silacyclohexyl)-1-butyne-3-ol from 4-ethynyl-2,3,3',4',5'-pentafluoro-4-biphenyl and 4-pentyl-4-silacyclohexylacetaldehyde, (P23) 1-(2,6,3',4',5'-pentafluoro-4-biphenyl)-4-(trans-4-propyl-4-silacyclohexyl)-1-butyne-3-ol from 4-ethynyl-2,6,3',4',5'-pentafluoro-4-biphenyl and 4-propyl-4-silacyclohexylacetaldehyde, (P24) 1-(trans-4-(4-fluorophenyl)cyclohexyl)-4-(trans-4-(trans-4-pentyl-4-silacyclohexyl)cyclohexyl)-1-butyne-3-ol from 4-(4-ethynylcyclohexyl)fluorobenzene and 4-(4-pentyl-4-silacyclohexyl)cyclohexylacetaldehyde, (P25) 1-(trans-4-(3,4-difluorophenyl)cyclohexyl)-4-(trans-4-(trans-4-pentyl-4-silacyclohexyl)cyclohexyl)-1-butyne-3-ol from 1,2-difluoro (4-ethynylcyclohexyl)benzene and 4-pentyl-4-silacyclohexylacetaldehyde, (P26) 1-(4'-fluoro-4-biphenyl)-4-(trans-4-(trans-4-pentyl-4-silacyclohexyl)cyclohexyl)-1-butyne-3-ol from 4-ethynyl-4'-fluorobiphenyl and 4-pentyl-4-silacyclohexylacetaldehyde, (P27) 1-(2,3,3',4'-tetrafluoro-4-biphenyl)-4-(trans-4-(trans-4-propyl-4-silacyclohexyl)cyclohexyl)-1-butyne-3-ol from 4-ethynyl-2,3,3',4'-tetrafluorobiphenyl and 4-propyl-4-silacyclohexylacetaldehyde, (P28) 1-(4'-fluoro-4-biphenyl)-4-(4-(trans-4-pentyl-4-silacyclohexyl)phenyl)-1-butyne-3-ol from 4-ethynyl-4'-fluorobiphenyl and 4-pentyl-4-silacyclohexylacetaldehyde, (P29) 1-(4'-trifluoromethoxy-2,6,3'-trifluoro-4-biphenyl)-4-(4-(trans-4-propyl-4-silacyclohexyl)-2-fluorophenyl)-1-butyne-3-ol from 4-ethynyl-4'-trifluoromethoxy-2,6,3'-trifluorobiphenyl and 4-(4-propyl-4-silacyclohexyl)-2-fluorophenylacetaldehyde, (P30) 1-(2,3',4'-trifluoro-4-biphenyl)-4-(4-(trans-4-propyl-4-silacyclohexyl)-2-fluorophenyl)-1-butyne-3-ol from 4-ethynyl-2,3',4'-trifluorofluorobiphenyl and 4-(4-propyl-4-silacyclohexyl)-2-fluorophenylacetaldehyde, and (P31) 1-(4-cyanophenyl)-4-(trans-4-propyl-4-silacyclohexyl)-1-butyne-3-ol from 4-ethynylbenzonitrile and 4-propyl-4-silanocyclohexylacetaldehyde.

Further, the following compounds could be produced by selecting suitable starting materials in the method illustrated in Example 2. Accordingly, the products are (P32) 1-(4-cyanophenyl)-4-(trans-4-propyl-4-silacyclohexyl)-3E-butene-1-yne from 1-(4-cyanophenyl)-4-(trans-4-propyl-4-silacyclohexyl)-1-butyne-3-ol, (P33) 1-(4-chlorophenyl)-4-(trans-4-propyl-4-silacyclohexyl)-3E-butene-1-yne from 1-(4-chlorophenyl)-4-(trans-4-propyl-4-silacyclohexyl)-1-butyne-3-ol, (P34) 1-(4-trifluoromethylphenyl)-4-(trans-4-heptyl-4-silacyclohexyl)-3E-butene-1-yne from 1-(4-trifluoromethylphenyl)-4-(trans-4-heptyl-4-silacyclohexyl)-1-butyne-3-ol, (P35) 1-(4-trifluoromethoxyphenyl)-4-(trans-4-propyl-4-silacyclohexyl)-3E-butene-1-yne from 1-(4-trifluoromethoxyphenyl)-4-(trans-4-propyl-4-silacyclohexyl)- 1-butyne-3-ol, (P36) 1-(4-methoxyphenyl)-4-(trans-4-propyl-4-silacyclohexyl)-3E-butene-1-yne from 1-(4-methoxyphenyl)-4-(trans-4-propyl-4-silacyclohexyl)-1-butyne-3-ol, (P37) 1-(3,4-difluorophenyl)-4-(trans-4-propyl-4-fluoro-4-silacyclohexyl)-3E-butene-1-yne from 1-(3,4-difluorophenyl)-4-(trans-4-propyl-4-fluoro-4-silacyclohexyl)-1-butyne-3-ol, (P38) 1-(3-fluoro-4-trifluoromethoxyphenyl)-4-(trans-4-propyl-4-methyl-4-silacyclohexyl)-3E-butene-1-yne from 1-(3-fluoro-4-trifluoromethoxyphenyl)-4-(trans-4-propyl-4-methyl-4-silacyclohexyl)-1-butyne-3-ol, (P39) 1-(4-methylphenyl)-4-(trans-4-(5-methoxypentyl)-4-silacyclohexyl)-3E-butene-1-yne from 1-(4-methylphenyl)-4-(trans-4-(5-methoxypentyl)-4-silacyclohexyl)-1-butyne-3-ol, (P40) 1-(3,4-difluorophenyl)-4-(trans-4-(4-pentenyl)-4-silacyclohexyl)-3E-butene-1-yne from 1-(3,4-difluorophenyl)-4-(trans-4-(4-pentenyl)-4-silacyclohexyl)-1-butyne-3-ol, (P41) 1-(3-fluoro-4-cyanophenyl)-4-(trans-4-(3-methylbutyl)-4-silacyclohexyl)-3E-butene-1-yne from 1-(3-fluoro-4-cyanophenyl)-4-(trans-4-(3-methylbutyl)-4-silacyclohexyl)-1-butyne-3-ol, (P42) 1-(3-fluoro-4-trifluoromethylphenyl)-4-(trans-4-(4,4-difluorobutyl)-4-silacyclohexyl)-3E-butene- 1-yne from 1-(3-fluoro-4-trifluoromethylphenyl)-4-(trans-4-(4,4-difluorobutyl)-4-silacyclohexyl)-1-butyne-3-ol, (P43) 1-(3-fluoro-4-trifluoromethoxyphenyl)-4-(trans-4-(4-fluoropentyl)-4-silacyclohexyl)-3E-butene-1-yne from 1-(3-fluoro-4 -trifluoromethoxyphenyl)-4-(trans-4-(4-fluoropentyl)-4-silacyclohexyl)-1-butyne-3-ol, (P44) 1-(3-fluoro-4-difluoromethoxyphenyl)-4-(trans-4-(4,4-difluoropropyl)-4-silacyclohexyl)-3E-butene-1-yne from 1-(3-fluoro-4-difluoromethoxyphenyl)-4-(trans-4-(4,4-difluoropropyl)-4-silacyclohexyl)-1-butyne-3-ol, (P45) 1-(4-fluorophenyl)-4-(trans-4-(trans-4-pentyl-4-silacyclohexyl)cyclohexyl)-3E-butene-1-yne from 1-(4-fluorophenyl)-4-(trans-4-(trans-4-pentyl-4-silacyclohexyl)cyclohexyl)-1-butyne-3-ol, (P46) 1-(2,3-difluoro-4-trifluoromethylphenyl)-4-(trans-4-(transheptyl-4-silacyclohexyl)cyclohexyl)-3E-butene-1-yne from 1-(2,3-difluoro-4-trifluoromethylphenyl)-4-(trans-4-heptyl-4-silacyclohexyl)cyclohexyl)-1-butyne-3-ol, (P47) 1-(4-fluorophenyl)-4-(4-(trans-4-pentyl-4-silacyclohexyl)phenyl)-3E-butene-1-yne from 1-(4-fluorophenyl)-4-(4-(trans-4-pentyl-4-silacyclohexyl)phenyl)-1-butyne-3-ol, (P48) 1-(3,4,5-trifluorophenyl)-4-(4-(trans-4-heptyl-4-silacyclohexyl)phenyl)-3E-butene-1-yne from 1-(3,4,5-trifluorophenyl)-4-(4-(trans-4-heptyl-4-silacyclohexyl)phenyl)-1-butyne-3-ol, (P49) 1-(trans-4-(4-fluorophenyl)cyclohexyl)-4-(trans-4-pentyl-4-silacyclohexyl)-3E-butene-1-yne from 1-(trans-4-(4-fluorophenyl)cyclohexyl)-4-(trans-4-pentyl-4-silacyclohexyl)-1-butyne-3-ol, (P50) 1-(trans-4-(3,5-difluoro-4-trifluoromethylphenyl)cyclohexyl)-4-(trans-4-heptyl-4-silacyclohexyl)-3E-butene-1-yne from 1 -(trans-4-(3,5-difluoro-4-trifluoromethylphenyl)cyclohexyl)-4-(trans-4-heptyl-4-silacyclohexyl)-1-butyne-3-ol, (P51) 1-(4'-fluoro-4-biphenyl)-4-(trans-4-pentyl-4-silacyclohexyl)-3E-butene-1-yne from 1-(4'-fluoro-4-biphenyl)-4-(trans-4-pentyl-4-silacyclohexyl)-1-butyne-3-ol, (P52) 1-(2,3',5'-trifluoro-4'-trifluoromethoxy-4-biphenyl)-4-(trans-4-pentyl-4-silacyclohexyl)-3E-butene-1-yne from 1-(2,3',5'-trifluoro-4'-trifluoromethoxy-4-biphenyl)-4-(trans-4-pentyl-4-silacyclohexyl)-1-butyne-3-ol, (P53) 1-(2,3,3',4',5'-pentafluoro-4-biphenyl)-4-(trans-4-pentyl-4-silacyclohexyl)-3E-butene-1-yne from 1-(2,3,3',4',5'-pentafluoro-4-biphenyl)-4-(trans-4-pentyl-4-silacyclohexyl)-1-butyne-3-ol, (P54) 1-(2,6,3',4',5'-pentafluoro-4-biphenyl)-4-(trans-4-propyl-4-silacyclohexyl)-3E-butene-1-yne from 1-(2,6,3',4',5'-pentafluoro-4-biphenyl)-4-(trans-4-propyl-4-silacyclohexyl)-1-butyne-3-ol, (P55) 1-(trans-4-(4-fluorophenyl)cyclohexyl-4-(trans-4-(trans-4-pentyl-4-silacyclohexyl)cyclohexyl)-3E-butene-1-yne from 1-(trans-4-(4-fluorophenyl)cyclohexyl-4-(trans-4-(trans-4-pentyl-4-silacyclohexyl)cyclohexyl)-1-butyne-3-ol, (P56) 1-(trans-4-(3,4-difluorophenyl)cyclohexyl-4-(trans-4-(trans-4-pentyl-4-silacyclohexyl)cyclohexyl)-3E-butene-1-yne from 1-(trans-4-(3,4-difluorophenyl)cyclohexyl)-4-(trans-4-(trans-4-pentyl-4-silacyclohexyl)cyclohexyl)-1-butyne-3-ol, (P57) 1-(4'-fluoro-4-biphenyl)-4-(trans-4-(trans-4-pentyl-4-silacyclohexyl)cyclohexyl)-3E-butene-1-yne from 1-(4'-fluoro-4-biphenyl)-4-(trans-4-(trans-4-pentyl-4-silacyclohexyl)cyclohexyl)-1-butyne-3-ol, (P58) 1-(2,3,3',4'-tetrafluoro-4-biphenyl)-4-(trans-4-(trans-4-propyl-4-silacyclohexyl)cyclohexyl)-3E-butene-1-yne from 1-(2,3,3',4'-tetrafluoro-4-biphenyl)-4-(trans-4-(trans-4-propyl-4-silacyclohexyl)cyclohexyl)-1-butyne-3-ol, (P59) 1-(4'-fluoro-4-biphenyl)-4-(4-(trans-4-pentyl-4-silacyclohexyl)phenyl)-3E-butene-1-yne from 1-(4'-fluoro-4-diphenyl)-4-(4-(trans-4-pentyl-4-silacyclohexyl)phenyl)-1-butyne-3-ol, (P60) 1-(4'-trifluoromethoxy-2,6,3'-trifluoro-4-biphenyl)-4- (4-(trans-4-propyl-4-silacyclohexyl)-2-fluorophenyl)-3E-butene-1-yne from 1-(4'-trifluoromethoxy2,6,3'-trifluoro-4-biphenyl)-4-(4-(trans-4-propyl-4-silacyclohexyl)-2-fluorophenyl)-1-butyne-3-ol, and (P61) 1-(2,3'4'-trifluoro-4-biphenyl)-4-(4-(trans-4-propyl-4-silacyclohexyl)-2-fluorophenyl)-3E-butene-1-yne from 1-(2,3'4'-trifluoro-4-biphenyl)-4-(4-(trans-4-propyl-4-silacyclohexyl)-2-fluorophenyl)-1-butyne-3-ol.

The compounds of the present invention that were produced, as specified above, were added to existing liquid crystals to produce the liquid crystal compositions of the present invention. The liquid crystal compositions thus obtained were examined for their viscosity at 20° C.

The compounds of the present invention not illustrated above can also be easily produced by those skilled in the art on the basis of the description of the present specification.

Examples of liquid crystal compositions

Mixture A consisting of 40 mol % 4-(4-(trans-4-ethylcyclohexyl)-trans-4-cyclohexyl)-1, 2-difluorobenzene, 35 mol-% 4-(4-(trans-4-n-propylcyclohexyl)-trans-4-cyclohexyl)-1,2-difluorobenzene, and 25 mol-% 4-(4-trans-4-n-pentylcyclohexyl)-trans-4-cyclohexyl)-1, 2-difluorobenzene had the following properties:

C-N transition temperature: 7° C.
N-I transition temperature: 106° C.
Viscosity (20° C.): 26 cp.

A mixture consisting of 85% by weight of said mixture A and 15% by weight of 1-(4-fluorophenyl)-4-(trans-4-pentyl-4-silacyclohexyl)-3E-butene-1-yne obtained in Example 2 had the following properties:

C-N transition temperature: 5.5° C.
N-I transition temperature: 95.6° C.
Viscosity (20° C): 21.5 cp.

We claim:

1. A silacyclohexane compound represented by the general formula (I):

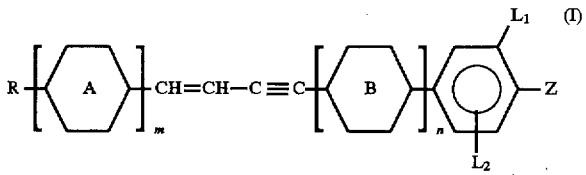

wherein R represents a straight-chain alkyl group having 1 to 10 carbon atoms, a mono or difluoro alkyl group having 1 to 10 carbon atoms, a branched-chain alkyl group having 3 to 8 carbon atoms, a alkoxyalkyl group having 2 to 7 carbon atoms, and a alkenyl group having 2 to 8 carbon atoms;

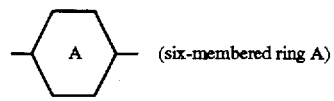

and

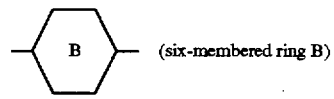

are groups selected from the group consisting of a trans-1-sila-1,4-cyclohexylene group and a trans-4-sila-1,4-cyclohexylene group both having a substituent group H, F, Cl, CH₃ or Ar (Ar stands for a phenyl or tolyl group) on silicon at the 1 or 4 position, a trans-1,4-cyclohexylene group, and

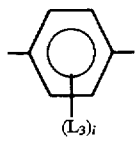

provided that at least one group of said six-membered ring A and said six-membered ring B is the trans-1-sila-1,4-cyclohexylene or trans-4-sila-1,4-cyclohexylene group having the substituent group H, F, Cl, CH₃ or Ar (Ar stands for a phenyl or tolyl group) on silicon at the 1 or 4 position; Z represents CN, F, Cl, CF₃, CClF₂, CHClF, OCF₃, OCClF₂, OCHF₂, OCHClF, R, or OR group; L₁ represents H, F or Cl; L₂ and L₃ stand independently for H or F; i represents an integer of 0 to 2; m is 1 or 2; n is 0 or 1; and if m is 2, the two rings are independent and may be the same or different.

2. A silacyclohexane compound claimed in claim 1, wherein the six-membered ring A and the six-membered ring B of the general formula (I) are groups selected from the group consisting of a trans-1-sila-1,4-cyclohexylene group and a trans-4-sila-1,4-cyclohexylene group both having a substituent group H, F, Cl, or CH₃ on silicon at the 1 or 4 position, a trans-1,4-cyclohexylene group, and

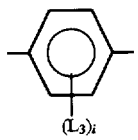

provided that at least one group of the six-membered ring A and the six-membered ring B is the trans-1-sila-1,4-cyclohexylene or trans-4-sila-1,4-cyclohexylene group having the substituent group H, F, Cl, or CH₃ on silicone at the 1 or 4 position.

3. A process for producing the silacyclohexane compound claimed in claim 1, which comprises a carbon-carbon bond forming reaction between an organometallic reagent represented by the following formula:

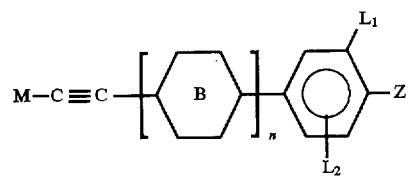

wherein M represents MgP or Li where P is a halogen atom and a compound represented by the following formula:

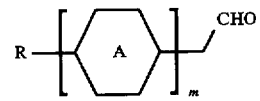

the product of which undergoes a hydrolysis reaction to form an alcohol compound represented by the following formula:

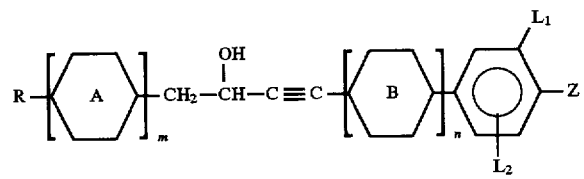

followed by a dehydration reaction of said alcohol compound to form said silacyclohexane compound.

4. A liquid crystal composition comprising the silacyclohexane compound claimed in claim 1.

5. A liquid crystal display element comprising the liquid crystal composition claimed in claim 4.

* * * * *